United States Patent [19]
Kadelka et al.

[11] Patent Number: 4,588,833
[45] Date of Patent: May 13, 1986

[54] PROCESS FOR THE PREPARATION OF SUBSTITUTED SUCCINIC ACID AMIDES

[75] Inventors: Jürgen Kadelka; Hans-Helmut Schwarz, both of Krefeld, Fed. Rep. of Germany

[73] Assignee: Bayer Aktiengesellschaft, Leverkusen, Fed. Rep. of Germany

[21] Appl. No.: 665,226

[22] Filed: Oct. 26, 1984

[30] Foreign Application Priority Data

Oct. 29, 1983 [DE]  Fed. Rep. of Germany ....... 3339386
May 30, 1984 [DE]  Fed. Rep. of Germany ....... 3420112

[51] Int. Cl.$^4$ ........................................... C07C 102/00
[52] U.S. Cl. ..................................... 560/145; 560/41; 560/43; 560/114; 560/139; 560/155; 560/173; 562/406; 562/497; 562/522; 562/553; 564/132
[58] Field of Search ................ 560/173, 233, 204, 41, 560/43, 130, 155, 114, 139, 145; 564/155, 160; 562/406, 497, 522, 553, 574

[56] References Cited

U.S. PATENT DOCUMENTS

| | | | |
|---|---|---|---|
| 2,542,767 | 2/1951 | Gresham | 560/233 |
| 2,689,261 | 9/1954 | Reppe | 560/233 |
| 2,768,968 | 10/1956 | Reppe | 560/233 |
| 3,437,676 | 4/1969 | Kutepow | 560/204 |
| 3,507,891 | 4/1970 | Hearne | 560/233 |
| 3,980,683 | 9/1976 | Isa | 560/233 |
| 4,303,589 | 12/1981 | Chen | 560/233 |
| 4,331,612 | 5/1982 | Pesa | 560/233 |
| 4,435,575 | 3/1984 | Cainelli | 560/204 |

OTHER PUBLICATIONS

Falbe, "Carbon Monoxide in Organic Synthesis," pp. 78–87 & 106–118 (1970).

Primary Examiner—Michael L. Shippen
Attorney, Agent, or Firm—Sprung Horn Kramer & Woods

[57] ABSTRACT

Substituted succinic acid amides, in particular substituted succinic acid amides containing differing derivative groups, are prepared by reacting unsaturated carboxamides with carbon monoxide and with a nucleophilic component containing at least one mobile hydrogen atom, in the presence of cobalt compounds and, if appropriate, in the presence of one or more tertiary nitrogen bases, under an elevated pressure and at an elevated temperature.

20 Claims, No Drawings

PROCESS FOR THE PREPARATION OF SUBSTITUTED SUCCINIC ACID AMIDES

The invention relates to a process for the preparation of substituted succinic acid amides, in particular for the preparation of substituted succinic acid amides containing differing derivative groups, by reacting suitable carboxamides with carbon monoxide and with a nucleophilic component containing at least one mobile hydrogen atom, in the presence of cobalt compounds and, if appropriate, in the presence of one or more tertiary nitrogen bases, under an elevated pressure and at an elevated temperature.

It is known from J. Chem. Soc. 1953, 3490, that 2-substituted succinic acid ester-anilides are obtained starting from correspondingly substituted N-phenylsuccinic acid imides, by hydrolytic cleavage and subsequent esterification. This method is involved, since it contains several reaction stages. Moreover, the separation of the isomeric half-derivatives obtained by hydrolysis gives rise to great difficulties. Additionally, the yields are low, depending on which isomer is to be synthesised.

Another method, to prepare, for example, 2-methylsuccinic acid 1-ester-4-amide, is described in J. Amer. Chem. Soc. 81, 4946 (1959). The hydrogenation of β-carboxycrotonamide gives the half-amide of methylsuccinic acid, and subsequent esterification of the latter results in the desired reaction product. A disadvantage in this method is the number of reaction stages as well the accessibility of the unsaturated carboxylic acid derivates employed as starting materials.

It is also known that carboxylic acids or carboxylic acid derivatives can be prepared by reacting olefins with carbon monoxide and an H-acid component, such as water, an alcohol or an amine, in the presence of a catalyst containing a metal of the 8th sub-group of the periodic system of the elements (J. Falbe, Synthesen mit Kohlenmonoxid ("Syntheses using Carbon Monoxide"), Springer-Verlag, Berlin, Heidelberg, New York 1967).

The hydrocarboxylation of crotonic acid in the presence of cobalt carbonyl in acetone as solvent gives a mixture of glutaric and methylsuccinic acid which has not been quantified precisely (Chim. Ind. 37, 1029 (1955); CA volume 50, 11,239). The yields achieved are only moderate; in addition, the two components of the product mixture each have the same functional end group.

Dicarboxylic acid diesters containing mixed functional groups can be synthesised in accordance with EP-OS (European Published Specification) No. 80,957 by reacting α,β-unsaturated carboxylic acid esters with carbon monoxide and an alcohol in the presence of cobalt catalysts and tertiary aromatic nitrogen bases. However, this method results in linear dicarboxylic acid derivatives.

A process has now been found for the preparation of substituted succinic acid amides of the formula

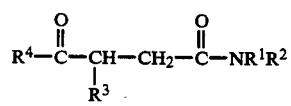 (I)

wherein
$R^1$ and $R^2$ can be identical or different and represent hydrogen, an alkyl or cycloalkyl radical having 1 to 20 carbon atoms or an aralkyl radical having 7 to 20 carbon atoms or an aryl radical having 6 to 14 carbon atoms, the alkyl, cycloalkyl, aralkyl or aryl radical concerned being optionally monosubstituted or polysubstituted by an alkyl and/or alkoxy group having 1 to 6 carbon atoms and/or by fluorine, chlorine, bromine and/or iodine and/or by an alkyl and/or alkoxy group which has 1 to 6 carbon atoms and is monosubstituted or polysubstituted by fluorine, chlorine, bromine and/or iodine, $R^3$ represents an unbranched or branched, substituted or unsubstituted alkyl radical having 1 to 28 carbon atoms and $R^4$ represents $-OR^5$ and $-NR^5R^6$, $R^5$ and $R^6$ being identical or different and having the meaning indicated for $R^1$ and $R^2$, which is characterized in that unsaturated carboxamides of the formula $$R^7-CO-NR^1R^2 \qquad (II)$$

wherein
$R^1$ and $R^2$ have the meaning indicated above and
$R^7$ represents an α,β-unsaturated or β,γ-unsaturated unbranched or branched, substituted or unsubstituted alkyl radical having 3 to 30 carbon atoms, are reacted with H-acid nucleophilic compounds of the formula $$HX \qquad (III)$$

wherein
$X$ represents $-OR^5$ and $-NR^5R^6$ and
$R^5$ and $R^6$ have the abovementioned meaning,
with carbon monoxide in the presence of cobalt compounds and, if appropriate, in the presence of one or more tertiary nitrogen bases under an elevated pressure and at an elevated temperature.

Substituted succinic acid amides which contain differing derivative groups and have the formula

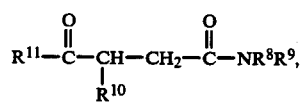 (IV)

wherein
$R^8$ and $R^9$ can be identical or different and have the same meaning as $R^1$ and $R^2$,
$R^{10}$ has the same meaning as $R^3$ and $R^{11}$ has the same meaning as $R^4$, subject to the proviso that, in the case of a diamide, the amide groups must not be identical, can be obtained, in particular with a high degree of selectivity, by the process according to the invention.

Substituted succinic acid amides containing differing derivative groups and having the formulae

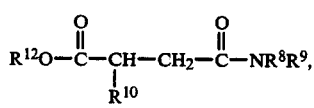 (V)

and

-continued

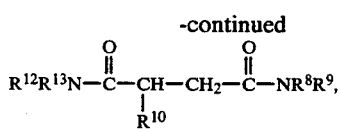

wherein
R$^{12}$ and R$^{13}$ can be identical or different and have the meaning indicated for R$^1$ and R$^2$ and R$^8$, R$^9$ and R$^{10}$ have the abovementioned meaning, subject to the proviso that in formula VI the amide radicals NR$^{12}$R$^{13}$ and NR$^8$R$^9$ are different, are obtained particularly preferentially.

Suitable α,β-olefinically unsaturated or β,γ-olefinically unsaturated, unbranched or branched, substituted or unsubstituted alkyl radicals R$^7$ are, in particular, radicals having 3 to 10 carbon atoms, such as prop-1-en-1-yl, prop-2-en-1-yl, but-1-en-1-yl, but-2-en-1-yl, pent-1-en-1-yl, pent-2-en-1-yl, hex-1-en-1-yl, hex-2-en-1-yl, hept-1-en-1-yl, oct-1-en-1-yl, non-1-en-1-yl, dec-1-en-1-yl, 2-methylprop-1-en-1-yl, hept-3-en-3-yl, 3-chloroprop-1-en-1-yl, 3-bromoprop-1-en-1-yl, 3-phenylprop-1-en-1-yl, and 3-phenylprop-2-en-1-yl, preferably prop-1-en-1-yl, prop-2-en-1-yl, but-1-en-1-yl, but-2-en-1-yl, oct-1-en-1-yl, 3-bromo-prop-1-en-1-yl and 3-phenylprop-1-en-1-yl.

Suitable alkyl radicals R$^1$ and R$^2$ of the formula (I) are preferentially those having 1 to 12 carbon atoms, such as the methyl, ethyl, n-propyl, isopropyl, n-butyl, isobutyl, 2-ethylhexyl, n-heptyl and decyl radical, preferably the methyl, ethyl, n-propyl and n-butyl radical, while suitable cycloalkyl radicals are preferentially those having 6 to 12 carbon atoms, such as the cyclohexyl, cyclooctyl and cyclododecyl radical, preferably the cyclohexyl radical, and suitable aralkyl radicals are preferentially those having 7 to 12 carbon atoms, such as the benzyl, 1-phenyleth-1-yl and 2-phenyleth-1-yl radical, preferably the benzyl radical, and suitable aryl radicals are preferentially those having 6 to 10 carbon atoms, such as the phenyl or naphthyl radical, preferably the phenyl radical.

The alkyl, cycloalkyl, aralkyl and aryl radicals R$^1$ and R$^2$ can also be substituted, additionally, by one or more alkyl and/or alkoxy groups having 1 to 6 carbon atoms and/or by fluorine, chlorine, bromine and/or iodine and/or by an alkyl and/or alkoxy group which is monosubstituted or polysubstituted by fluorine, chlorine, bromine and/or iodine, preferably by methyl, ethyl, methoxy, ethoxy and/or trifluoromethyl groups and by fluorine and or chlorine. The following may be mentioned as examples of possible radicals containing such substituents: 2-methoxyethyl, 2-ethoxyethyl, o-, m- or p-cresyl, o-, m- or p-chlorophenyl, o-, m- or p-fluorophenyl, 3,5-dimethylphenyl, 3,5-dichlorophenyl, pentafluorophenyl and 3,5-bis(trifluoromethyl)-phenyl.

The following or α,β-olefinically unsaturated or β,γ-olefinically unsaturated carboxylic acid derivatives can, for example, accordingly be employed in the process according to the invention: the methylamides, ethylamides, dimethylamides, diethylamides, diphenylamides, benzylamides, dibenzylamides, N-methylbenzylamides, N-ethylbenzylamides, anilides, N-methylanilides, N-ethylanilides, N-benzylanilides, 3,5-dichloroanilides and 3,5-dimethylanilides of crotonic acid, pent-2-enoic acid, pent-3-enoic acid, hex-2-enoic acid, hex-3-enoic acid, non-2-enoic acid, 3-bromocrotonic acid and 3-phenylcrotonic acid.

H-acid nucleophilic compounds of the formula (III) which can be employed in the process according to the invention are water, aliphatic and aromatic alcohols, ammonia and aliphatic and aromatic amines. The alcohol or amine which is employed as the H-acid nucleophilic component in the process according to the invention depends on the succinic acids containing differing derivative groups and substituted in the 2-position which are to be prepared. Thus, it is possible to employ, as substituted aliphatic or cycloaliphatic alcohols, R$^5$OH, which are optionally monosubstituted or polysubstituted by an alkyl and/or alkoxy group having 1 to 6 carbon atoms and/or by fluorine, chlorine, bromine and/or iodine, alcohols in which the radical R$^5$ contains 1 to 20 carbon atoms, preferably 1 to 12 carbon atoms, such as methyl, ethyl, n-propyl, isopropyl, n-butyl, isobutyl, n-pentyl, n-hexyl, n-heptyl, n-octyl, n-oct-2-yl, n-decyl, cyclohexyl, cyclooctyl and cyclododecyl.

2-Methoxyethanol, 2-ethoxyethanol, 2-n-butoxyethanol, 2-chloroethanol, 1-, 2-, 3- or 4-methylcyclohexanol and 2-chlorocyclohexanol may be mentioned as examples of substituted alcohols which can be employed.

It is possible to employ, as substituted arylaliphatic or aromatic alcohols, R$^3$OH, which are optionally monosubstituted or polysubstituted by an alkyl and/or alkoxy group having 1 to 6 carbon atoms and/or by fluorine, chlorine, bromine and/or iodine, alcohols in which the radical R$^3$ contains 6 to 18 carbon atoms, preferably 6 to 12 carbon atoms, such as the benzyl, 1-phenyleth-1-yl, 2phenyleth-1-yl, phenyl and naphthyl radical.

o-, m- and p-cresol, 2,3-, 2,4-, 2,5-, 2,6- and 3,5-xylenol, o-, m- and p-chlorophenol, o-, m- and p-fluorophenol, 4-methoxyphenol, 6-bromo-α-naphthol, 6-bromo-β-naphthol, 2-methoxy-4-n-propylphenol, p-chlorobenzyl alcohol, p-fluorobenzyl alcohol and pentafluorobenzyl alcohol may be mentioned as examples of alcohols containing a substituted aryl radical which can be employed.

As well as ammonia, the following are examples of aliphatic or aromatic amines containing at least one mobile hydrogen atom on the nitrogen which can be employed: methylamine, ethylamine, n-propylamine, isopropylamine, n-butylamine, isobutylamine, benzylamine, dimethylamine, diethylamine, n-butylmethylamine, dibenzylamine, cyclohexylamine, N-methylcyclohexylamine, N-ethylcyclohexylamine or aniline or substituted anilines, such as N-methylaniline, N-ethylaniline, N-benzylaniline, o-, m- and p-chloroaniline, o-, m- and p-fluoroaniline, o-, m- and p-methylaniline, 2,4-, 2,6- and 3,5-dimethylaniline, 2,3-, 2,4-, 2,6-, 3,4- and 3,5-dichloroaniline, 2,4,5-trichloroaniline, 2,4,6-trichloroaniline and 3,5-bis-(trifluoromethyl)-aniline. It is also possible to use diols and alcohols of higher functionality, such as ethylene glycol, 1,3-propanediol, 1,4-butanediol, trimethylolpropane and pentaerythritol, and also diamines and amines of higher functionality having at least one mobile hydrogen atom on the nitrogen, such as ethylenediamine or hexamethylenediamine.

The conversion of the rated or α,β-unsaturated or β,γ-unsaturated carboxamides of the formula (II) which are employed as the substrates is about 60 to 100%, as a rule. On the other hand, it would be immaterial as far as the process according to the invention is concerned, if the conversion of the substrate were limited to figures less than 60%.

It can also be expedient to carry out the reaction in the presence of an inert organic solvent or diluent. For example, the reaction according to the invention can be carried out in the presence of toluene, tetrahydrofuran, dioxane, acetonitrile and/or di-n-butyl ether. The amount of inert solvent and/or diluent to be employed is not critical and can, if necessary, be determined readily by a few preliminary tests.

The amount of H-acid nucleophilic compound of the general formula (II) to be employed should be at least equimolar, relative to the unsaturated carboxamide to be reacted. Amounts of nucleophilic component of about 1.05 to 5 mol/mol of unsaturated carboxamide have proved advantageous.

On the other hand, a fairly large excess does not impede the process according to the invention, since, in addition, the nucleophilic component can be used as the solvent and/or diluent in some reactions, as a result of which it is possible to dispense with the use of an extraneous solvent and/or diluent.

Carbon monoxide pressures of about 20 to 4,000 bar are used for the preparation of the substituted succinic acid amides. Carbon monoxide pressures of 50 to 1,000 bar have proved advantageous, pressures of 80 to 300 bar being particularly advantageous.

It is expedient in the process according to the invention to employ the carbon monoxide in excess, especially in a 2-molar to 100-molar excess, relative to the substrate to be reacted. Excess carbon monoxide can be removed from the other reactants easily, for example by releasing the pressure, after the reaction, and can be re-used as such.

In order to achieve acceptable reaction rates, it is beneficial to mix about 0.5 to 10% by volume of hydrogen, preferably 1 to 3% by volume of hydrogen, with the carbon monoxide.

The cobalt compounds employed as catalysts are carbonyl complexes or hydrocarbonyl complexes of cobalt. However, it is also possible to use chlorides, bromides, iodides, acetals, oxides, carbonates, sulphates or other cobalt compounds from which catalytically active cobalt carbonyl compounds are formed under the reaction conditions prevailing. On the other hand, it is also possible, when using cobalt compounds not containing carbonyl, for the actual reaction to be preceded by a so-called preforming stage, that is to say a specific pretreatment of the cobalt compound in order to generate the catalytically active compound. The cobalt compound which is employed preferentially is dicobalt octacarbonyl, $Co_2(CO)_8$. It is expedient to employ the cobalt carbonyl complexes in amounts such that about 1 to 200 mol of substrate, preferably 10 to 100 mol of substrate, are present per g-atom of cobalt. Substrate:cobalt ratios of 15 to 75:1 are particularly advantageous.

In some cases it can be advantageous for the process according to the invention to carry out the reaction in the presence of tertiary nitrogen bases, preferably aromatic tertiary nitrogen bases, having a $pK_A$ value of about 3 to 10, preferably of about 4 to 9. The presence of one or more nitrogen bases of this type can increase the selectivity of conversion to the substituted succinic acid amides in some cases. Whether an improvement in selectivity of conversion can be achieved by adding tertiary nitrogen bases of this type can be determined easily by a few preliminary tests.

Suitable nitrogen bases are, in particular, N-heterocyclic nitrogen compounds which are not substituted in the ortho-position relative to the hetero-atom. The following, for example, can be employed: pyridine, isoquinoline, β-picoline, γ-picoline, 3,5-lutidine, 4-ethylpyridine and/or 4-benzylpyridine, preferably pyridine, γ-picoline and/or isoquinoline.

In addition to nitrogen atoms, the bases to be employed can also contain other hetero-atoms, for example oxygen or chlorine.

It is usual to employ the nitrogen bases, which can be employed either individually or as a mixture with one another, and the unsaturated carboxamides, the substrate, in a molar ratio of about 0.001:1 to 1:1, preferably in a molar ratio of about 0.01:1 to 0.2:1. Higher concentrations of bases provide no economic advantages.

The reaction is carried out at a temperature of about 90° to 220° C., preferably 120° to 190° C. Depending on the substituted succinic acid amide which is to be synthesised, it is advisable to fix an upper limit to the reaction temperature, in order to prevent secondary reactions of the succinic acid amide, for example cyclization reactions. The optimum reaction temperature for a particular reaction can be determined easily by a few preliminary tests.

The reaction can be carried out either continuously or discontinuously.

Using as an example the reaction of crotonic acid diethylamide with carbon monoxide and methanol, the process according to the invention may be illustrated in terms of formulae as follows:

$$CH_3-CH=CH-\overset{O}{\underset{\|}{C}}-NEt_2 + CO + CH_3OH \xrightarrow[N-Base]{Co}$$

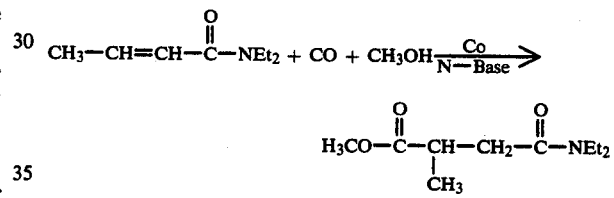

In general, the process according to the invention can be carried out as follows:

An autoclave which has been flushed with nitrogen or argon is charged with, for example, the alcohol, ammonia or the amine, if appropriate the tertiary nitrogen base(s), the cobalt catalyst, the unsaturated carboxylic acid derivative and, if appropriate, the inert solvent and/or diluent.

Carbon monoxide containing the required amount of hydrogen is then injected at room temperature in an amount such that the predetermined reaction pressure is built up at the desired reaction temperature. The contents of the autoclave are then heated to the reaction temperature and kept at this temperature (±3° C.), with stirring, for the predetermined time. The reaction pressure is kept constant, within a range of ±5 bar, during the reaction by successive replenishment of the reaction gas. The product mixture is then cooled, the autoclave is depressurised and the resulting reaction mixture is analyzed by gas chromatography, after the addition of a solvent if required. The product mixture can be worked up by distillation or crystallization in the manner customary in a particular case.

The following are examples of products which can be synthesized in a single reaction stage by the process according to the invention: 2-alkylsuccinic acid 1-alkylester-4-amides, 2-alkylsuccinic acid 1-cycloalkylester-4-amides, 2-alkylsuccinic acid 1-aralkylester-4-amides, 2-alkylsuccinic acid 1-arylester-4-amides and 2-alkylsuccinic acid 1-amide-4-amides (containing different amide radicals).

The substituted succinic acid amides, containing differing derivative groups, which are preferentially synthesised with the aid of the process according to the invention are for the most part new compounds. The following are mentioned as examples: 2-methylsuccinic acid 1-phenylester-4-diethylamide, 2-methylsuccinic acid 1-ethylester-4-diethylamide, 2-methylsuccinic acid 1-cyclohexyl ester-4-diethylamide, 2-methylsuccinic acid 1-(3,5-dichloroanilide)-4-diethylamide, 2-methylsuccinic acid 1-N-methylanilide-4-amide, 2-ethylsuccinic acid 1-ethylester-4-diethylamide and 2-methylsuccinic acid 1-[3,5-bis-(trifluoromethyl)-anilide]-4-diethylamide.

They are characterized by elementary analysis and/or IR spectrometry and/or proton nuclear resonance spectrometry.

The succinic acids substituted in the 2-position and containing differing derivative groups which are obtained by the process according to the invention are suitable for use as antioxidants in rubber compositions and as stabilizers in polymer materials, for example in polyesters, polycarbonates, polyestercarbonates, polyamides, polyurethanes, saturated and unsaturated polyolefines and in blends of these materials with one another. They can also be used as precursors in the synthesis of insecticides, fungicides, herbicides and acaricides and also pharmacological and physiological active compounds.

EXAMPLE 1

56.5 g of crotonic acid diethylamide, 56.5 g of phenol, 6.33 g of pyridine and 2.74 g of $Co_2(CO)_8$ were initially placed in a 0.25 liter shaking autoclave which had been flushed with nitrogen.

After the autoclave had been closed, sufficient carbon monoxide, containing approx. 2% by volume of hydrogen, was injected to give a total gas pressure of 150 bar when the reaction temperature was reached. The autoclave was then heated to 170° C. by means of an electrical heating element and was kept at this temperature for 45 minutes, during which shaking was continued. The reaction gas consumed was replaced by successive replenishment with fresh reaction gas, so that the reaction pressure was kept constant at 150 bar (±5 bar). When the reaction mixture had been cooled, the autoclave was depressurized and the product mixture was analysed by gas chromatography. Analysis showed that, relative to a 91.5 mol % conversion of crotonic acid diethylamide, 56.9 mol % of $C_5$-dicarboxylic acid derivatives containing differing derivative groups had been formed, 87.7% of which was 2-methylsuccinic acid 1-phenylester-4-diethylamide and 12.3% was glutaric acid phenylester-diethylamide.

2-Methylsuccinic acid 1-phenylester-4-diethylamide
Boiling point$_{0.3}$ = 155° C. $N_D^{20}$ = 1.5069.

Elementary analysis: found: 68.23% C, 8.10% H, 5.24% N, calculated: 68.41% C, 8.04% H, 5.32% N.

IR: $\nu C=0$ (ester) = 1758 cm$^{-1}$; $\nu C=0$ (amide) = 1641 cm$^{-1}$.

$_1$H-NMR: $\delta$ = 1.15 ppm (q, 6H); $\delta$ = 1.39 ppm (d, 3H), $\delta$ = 2.57 ppm, 2.81 ppm (2d, 2H); $\delta$ = 3.14 ppm (m, 1H), $\delta$ = 3.39 ppm (m, 4H); $\delta$ = 7.28 ppm (m, 5H).

EXAMPLE 2

56.5 g of crotonic acid diethylamide 36.9 g of ethanol, 1.27 g of pyridine and 2.74 g of $Co_2(CO)_8$ are reacted analogously to Example 1 for 1.5 hours at 170° C. under a carbon monoxide pressure of 150 bar (+approx. 2% by volume of hydrogen). Analysis showed that 99.6 mol % of the crotonic acid diethylamide had reacted. Relative to this, $C_5$-dicarboxylic acid derivatives containing mixed derivative groups had been formed at a selectivity of conversion of 97.4 mol %; 2-methylsuccinic acid 1-ethylester-4-diethylamide was 93.6% of this. In addition, butyric acid diethylamide and but-3-enoic acid diethylamide had been formed at selectivities of conversion of 1.2 mol % and 0.4 mol %, respectively.

2-Methylsuccinic acid 1-ethylester-4 -diethylamide
Boiling point$_{0.4}$ = 89°–91° C.; $n_D^{20}$ = 1.4507.

$^1$H-NMR: $\delta$ = 1.14 ppm (q, 6H) $\delta$ = 1.22 ppm (d, 3H); $\delta$ = 1.26 ppm (tr, 3H); $\delta$2.39 ppm, 2.68 ppm (2d, 2H); $\delta$ = 3.03 ppm (m, 1H); $\delta$ = 3.38 ppm (dq, 4H); $\delta$ = 4.13 ppm (q, 2H).

EXAMPLES 3 to 6

The results listed in Table 1 were obtained analogously to Example 2 under the conditions which are also stated in the table. The substrate employed in each case was 56.5 g ($\triangleq$ 0.4 mol) of crotonic acid diethylamide, the reaction time was 1.5 hours in each case and the reaction pressure was 150 bar in each case. Here and subsequently, the following definitions are used:

$$\text{Conversion C (mol \%)} = \frac{\text{moles of substrate reacted}}{\text{moles of substrate employed}} \times 100\%$$

$$\text{Selectivity S (mol \%)} = \frac{\text{moles of mixed dicarboxylic acid derivatives}}{\text{moles of substrate reacted}} \times 100\%$$

$I_1$ defines the portion of succinic acid, substituted in the 2-position and containing differing derivative groups, as a percentage of the total resulting dicarboxylic acids containing various derivative groups.

TABLE 1

| Example | Molar ratio in charge of: Substrate:EtOH:Pyridine:Co | | | | Temperature (°C.) | C (mol %) | S (mol %) | $I_1$ (%) |
|---|---|---|---|---|---|---|---|---|
| 3 | 25 | 50 | 5 | 1 | 170 | 95.3 | 92.2 | 91.5 |
| 4 | 25 | 50 | 0 | 1 | 170 | 99.5 | 96.4 | 94.0 |
| 5 | 25 | 50 | 5 | 1 | 150 | 40.7 | 63.2 | 92.6 |
| 6 | 50 | 100 | 1 | 1 | 170 | 99.6 | 83.7 | 92.1 |

EXAMPLE 7

70.6 g of crotonic acid diethylamide, 32.0 g of methanol, 7.9 g of pyridine and 3.42 g of $Co_2(CO)_8$ were reacted in accordance with Example 1 for 1.5 hours at 170° C. under a CO pressure of 150 bar (+2% of $H_2$). At a 58.9 mol % conversion of crotonic acid diethylamide, mixed $C_5$-dicarboxylic acid derivatives had been formed at a selectivity of conversion of 85.6 mol %, the proportion $I_1$ of 2-methylsuccinic acid 1-methylester-4-diethylamide being 91.5%.

2-Methylsuccinic acid 1-methylester-4-diethylamide

Boiling point$_{0.3}$ = 84° C.; $n_D^{20}$ = 1.4527.

$^1$H-NMR: $\delta$ = 1.14 ppm (q, 6H); $\delta$ = 1.23 ppm (d, 3H); $\delta$ = 2.41 ppm, 2.68 ppm (2d, 2H); $\delta$ = 2.99 ppm (m, 1H); $\delta$ = 3.34 ppm (dq, 4H); $\delta$ = 3.69 ppm (s, 3H).

EXAMPLE 8

56.5 g of crotonic acid diethylamide, 36.6 g of glycol monomethyl ether, 1.27 g of pyridine and 2.74 g of $Co_2N(CO)_8$ were reacted analogously to Example 1 for 1 hour at 170° C. under a CO pressure of 150 bar (+2% of H$_2$). At a complete conversion of the substrate, 84.4 mol % of C$_5$-dicarboxylic acid β-methoxyethylester-diethylamides had been formed, 91.6% of which were 2-methylsuccinic acid 1-β-methoxyethylester-4-diethylamide.

2-Methylsuccinic acid 1-β-methoxyethylester-4-diethylamide

Boiling point$_1$ = 125° C.; $n_D^{20}$ = 1.4548.

$^1$H-NMR: $\delta$ = 1.15 ppm (q, 6H); $\delta$ = 1.24 ppm (d, 3H); $\delta$ = 2.42 ppm, 2.69 ppm (2d, 2H); $\delta$ = 3.03 ppm (m, 1H); $\delta$ = 3.36 ppm (dq, 4H); $\delta$ = 3.41 ppm (s, 3H); $\delta$ = 3.60 ppm (tr, 2H); $\delta$ = 4.26 ppm (tr, 2H).

EXAMPLE 9

Example 8 was repeated, with the exceptions that 45.7 g of glycol monomethyl ether and 6.33 g of pyridine were employed and the reaction was carried out for 2 hours at 160° C. 42.8 mol % of the crotonic acid diethylamide reacted under these conditions. Relative to this, 65.4 mol % of C$_5$-dicarboxylic acids containing differing derivative groups were formed, the proportion I$_1$ being 90.7%.

EXAMPLE 10

Example 8 was repeated, with the exceptions that 48.1 g of cyclohexanol were employed instead of the glycol monomethyl ether. The reaction time was 0.5 hour. Analysis showed that the conversion of the crotonic acid diethylamide was 99.7 mol %, the selectivity of conversion to mixed dicarboxylic acid derivatives was 82.8 mol % and the proportion I$_1$ of 2-methylsuccinic acid 1-cyclohexylester-4-diethylamide was 92.1%.

2-Methylsuccinic acid 1-cyclohexylester-4-diethylamide

Boiling point$_{0.4}$ = 138° C.; $n_D^{20}$ = 1.4715

$^1$H-NMR: $\delta$ = 1.15 ppm (q, 6H); $\delta$ = 1.21 ppm (d, 3H); $\delta$ = 1.62 ppm (m, 10H); $\delta$ = 2.38 ppm, 2.68 ppm (2d, 2H); $\delta$ = 3.03 ppm (m, 1H); $\delta$ = 3.35 ppm (dq, 4H); $\delta$ = 4.77 ppm (m, 1H).

EXAMPLE 11

Example 10 was repeated, with the exception that 51.9 g of benzyl alcohol were employed instead of the cyclohexanol. The reaction temperature was 150° C. After 30 minutes, 98.2 mol % of crotonic acid diethylamide had reacted, from which 73.9 mol % of C$_5$-dicarboxylic acid benzylester-diethylamides had been formed, 92.0 mol % of which were 2-methylsuccinic acid 1-benzylester-4-diethylamide.

2-Methylsuccinic acid 1-benzylester-4-dimethylamide

Boiling point$_{0.4}$ = 171° C.; $N_D^{20}$ = 1.5054.

$^1$H-NMR: $\delta$ = 1.11 ppm (q, 6H); $\delta$ = 1.23 ppm (d, 3H); $\delta$ = 2.41 ppm, 2.69 ppm (2d, 2H); $\delta$ = 3.01 ppm (m, 1H); $\delta$ = 3.32 ppm (m, 4H); $\delta$ = 5.15 ppm (d, 2H); $\delta$ = 7.37 ppm (s, 5H).

EXAMPLE 12

Crotonic acid diethylamide was reacted with 64.9 g of p-cresol, analogously to Example 10. After 30 minutes, the conversion of substrate was 99.4 mol %, the selectivity S of conversion to mixed C$_5$-dicarboxylic acid derivatives was 76.6 mol % and the proportion I$_1$ of 2-methylsuccinic acid 1-p-cresylester-4-diethylamide was 91.6%.

2-Methylsuccinic acid 1-p-cresylester-4-diethylamide

Boiling point$_{0.35}$ = 163° C.; $n_D^{20}$ = 1.5056.

$^1$H-NMR: $\delta$ = 1.15 ppm (q, 6H); $\delta$ = 1.38 ppm (d, 3H); $\delta$ = 2.38 ppm (s, 3H); $\delta$ = 2.53 ppm, 2.78 ppm (2d, 2H); $\delta$ = 3.12 ppm (m, 1H); $\delta$ = 3.37 ppm (m, 4H); $\delta$ = 7.12 ppm (m, 4H).

EXAMPLE 13

42.4 g of crotonic acid diethylamide, 72.9 g of 3,5-dichloroaniline, 4.75 g of pyridine, 2.05 g of $Co_2(CO)_8$ and 43.2 g of tetrahydrofuran were reacted in accordance with Example 1 for 75 minutes at 150° C. under a CO pressure of 150 bar (+approx. 2% by volume of H$_2$).

At a conversion of crotonic acid diethylamide of 95.1 mol %, open-chain C$_5$-dicarboxylic acids containing mixed derivative groups had been formed at a selectivity S of conversion of 68.8 mol %, 90.1% of which were 2-methylsuccinic acid 1-(3,5-dichloroanilide)-4-diethylamide. 8.0 mol % of N-(3,5-dichlorophenyl)-2-methylsuccinimide had been formed as a further hydrocarboxylation product.

2-Methylsuccinic acid 1-(3,5-diichloroanilide)-4-diethylamide

Melting point = 124°-125° C. (10:1 petroleum ether-/ethanol).

$^1$H-NMR: $\delta$ = 1.14 ppm, 1.27 ppm (2tr, 6H); $\delta$ = 1.23 ppm (d, 3H); $\delta$ = 2.43 ppm, 2.87 ppm (2d, 2H); $\delta$ = 3.16 ppm (m, 1H); $\delta$ = 3.40 ppm (dq, 4H): $\delta$ = 6 92 ppm (tr, 1H); $\delta$ = 7.46 ppm (d, 2H); $\delta$ = 9.88 ppm (offset, brs, 1H).

EXAMPLE 14

Examples 13 was repeated, with the exceptions that 58.3 g of 3,5-dichloroaniline and 0.95 g of pyridine were employed and the reaction was carried out at 170° C. The conversion of substrate was 99.8 mol % and the selectivity of conversion to C$_5$-dicarboxylic acid 3,5-dichloroanilide-diethylamides was 67.8 mol % (I$_1$ = 85.8%) and of conversion to N-(3,5-dichlorophenyl)-2-methylsuccinimide was 23.4 mol %.

EXAMPLE 15

Example 8 was repeated, but 51.5 g of N-methylaniline were employed instead of the gylcol monomethyl ether. At a conversion of crotonic acid diethylamide of 60.7 mol %, relative to this, 68.7 mol % of mixed C$_5$-dicarboxylic acid derivatives were formed, of which the proportion I$_1$ of 2-methylsuccinic acid 1-N-methylanilide-4-diethylamide was 89.7%.

2-Methylsuccinic acid 1-N-methylanilide-4-diethylamide

Boiling point$_{0.7}$ = 158°-160° C.; $n_D^{20}$ = 1.5242.

$^1$H-NMR: $\delta$ = 1.05 ppm (q, 6H); $\delta$ = 1.22 ppm (d, 3H); $\delta$ = 2.19 ppm, 2.82 ppm (2d, 2H); $\delta$ = 3.04 ppm (m, 1H);

δ=3.27 ppm (s, 3H); δ=3.32 ppm (m, 4H); δ=7.42 ppm (m, 5H).

EXAMPLE 16

42.4 g of crotonic acid diethylamide, 103.1 g of 3,5-bis-(trifluoromethyl)-aniline, 4.75 g of pyridine, 2.05 g of $Co_2(CO)_8$ and 64.9 g of tetrahydrofuran were reacted in accordance with Example 1 for 2 hours at 160° C. under a CO pressure of 150 bar (+approx. 2% by volume of $H_2$).

At a conversion of crotonic acid diethylamide of 85.9 mol %, open-chain $C_5$-dicarboxylic acids containing mixed derivatives had been formed at a selectivity S of conversion of 57.5 mol %, 86.8% of these being 2-methylsuccinic acid 1-[3,5-bis-(trifluoromethyl)-anilide]-4-diethylamide. 26.7 mol % of N-[3,5-bis-(trifluoromethyl)phenyl]-2-methylsuccinimide had been formed as a further hydrocarboxylation product.

2-Methylsuccinic acid 1-[3,5-bis-(trifluoromethyl)-anilide]-4-diethylamide

Melting point=149°-150° C. (10:1 petroleum ether-/ethanol).

$^1$H-NMR: δ=1.14 ppm, 1.31 ppm (2tr, 6H); δ=1.29 ppm (d, 3H); δ=2.36 ppm, 3.01 ppm (2d, 2H); δ=3,23 ppm (m, 1H); δ=3.43 ppm (q, 4H); δ=7.18 ppm (s, 1H); δ=7.82 ppm (s, 2H); δ=9.90 ppm (offset, s, 1H).

EXAMPLE 17

56.4 g of crotonic acid diethylamide, 137.5 g of 3,5-bis-(trifluoromethyl)-aniline, 6.33 g of pyridine and 2.74 g of $Co_2(CO)_8$ were reacted analogously to Example 16 for 3 hours at 150° C. The conversion of substrate was 79.0 mol % and the selectivity of conversion to $C_5$-dicarboxylic acid 3,5-bis-(trifluoromethyl)-anilide-diethylamides was 26.5 mol % ($I_1$=86.8%) and of conversion to N-[3,5-bis-(trifluoromethyl)-phenyl]-2-methyl-succinimide was 5.1 mol %.

EXAMPLE 18

77.6 g of pent-3-enoic acid diethylamide, 32.2 g of ethanol, 1.58 g of pyridine and 3.42 g of $Co_2(CO)_8$ were reacted, as described in Example 1, for 1 hour at 170° C. under a carbon monoxide pressure of 150 bar (+approx. 2% by volume of $H_2$). After cooling, analysis indicated a conversion of pent-3-enoic acid diethylamide of 47.3 mol %. Relative to this, 61.5 mol % of $C_6$-dicarboxylic acid ethylester-diethylamides had been formed and these had the following composition: 64.6% (=$I_1$) of 2-ethylsuccinic acid 1-ethylester-4-diethylamide, 29.2% of 2-methylglutaric acid 1-ethylester-5-diethylamide and 6.2% of adipic acid ethylesterdiethylamide. Furthermore, as well as isomers of pentenoic acid diethylamide, n-pentanoic acid diethylamide and $C_6$-dicarboxylic acid bisdiethylamides (3 isomers) were formed at selectivities of conversion of 1.7 mol % and 1.1 mol %, respectively.

2-Ethylsuccinic acid 1-ethylester-4-diethylamide

Boiling point$_1$=117° C.; $n_D^{20}$=1.4516.

$^1$H-NMR: δ=0.96 ppm (tr, 3H); δ=1.15 ppm (q, 6H); δ=1.28 ppm (tr, 3H); δ=1.64 ppm (m, 2H); δ=2.42 ppm, 2.66 ppm (2d, 2H); δ=2.92 ppm (m, 1H); =3.36 ppm (q, 4H); δ=4.16 ppm (q, 2H).

EXAMPLE 19

Example 16 was repeated, with the exceptions that 4.75 g of pyridine were employed and the reaction time was 4 hours. A conversion of the substrate of 55.5 mol % was achieved; the selectivity S of conversion to mixed $C_6$-dicarboxylic acid derivatives was 42.2 mol % ($I_1$=62.8%).

EXAMPLE 20

The reaction was carried out analogously to Example 16, in the absence of pyridine. The conversion of pent-3-enoic acid diethylamide was 99.7 mol %. The selectivity S of conversion to $C_6$-dicarboxylic acid ethylester-diethylamides was 71.5 mol % ($I_1$=62.9%).

EXAMPLE 21

52.6 g of pent-3-enanilide, 19.2 g of methanol, 4.75 g of pyridine and 2.05 g of $Co_2(CO)_8$ were reacted analogously to Example 1 for 1.5 hours at 170° C. At a pentenanilide conversion of 58.3 mol %, $C_6$-dicarboxylic acid methylesteranilides were formed at a selectivity S of conversion of 37.5 mol % ($1_1$=65.3%).

What is claimed is:

1. A process for the preparation of a substituted succinic acid amide of the formula

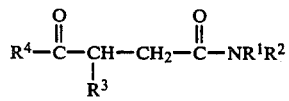

wherein
  $R^1$ and $R^2$ can be identical or different and represent hydrogen, an alkyl or cycloalkyl radical having 1 to 20 carbon atoms or an aralkyl radical having 7 to 20 carbon atoms or an aryl radical having 6 to 14 carbon atoms, the alkyl, cycloalkyl, aralkyl or aryl radical concerned being optionally monosubstituted or polysubtituted by an alkyl and/or alkoxy group having 1 to 6 carbon atoms and/or by fluorine, chlorine, bromine and/or iodine and/or by an alkyl and/or alkoxy group which has 1 to 6 carbon atoms and is monosubtituted or polysubstituted by fluorine, chlorine, bromine and/or iodine,
  $R^3$ represents an unbranched or branched, substituted or unsubstituted alkyl radical having 1 to 28 carbon atoms and
  $R^4$ represents —$OR^5$ and —$NR^5R^6$, $R^5$ and $R^6$ being identical or different and having the meaning indicated for $R^1$ and $R^2$, which comprises contacting an unsaturated carboxamide of the formula

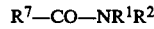

wherein
  $R^1$ and $R^2$ have the meaning indicated above and $R^7$ represents and α,β-unsaturated or β,γ-unsaturated, unbranched or branched, substituted or unsubstituted alkyl radical having 3 to 30 carbon atoms, with an H-acid nucleophilic compound of the formula

wherein
  X represents —$OR^5$ and —$NR^5R^6$ and
  $R^5$ and $R^6$ have the above-mentioned meaning, with carbon monoxide in the presence of a cobalt compound.

2. A process according to claim 1 wherein said H-acid nucleophilic compound is water, methanol, n- propanol, isopropanol, n-butanol, isobutanol, n-pentanol, n-hexanol, n-heptanol, n-octanol, n-octan-2-ol, n-decanol, cyclohexanol, cyclooctanol, cyclododecanol, 2-methoxyethanol, 2-ethoxyethanol, 2-n-butoxyethanol, 2-chloroethanol, 1-, 2-, 3- or 4-methylcyclohexanol, 2-chlorocyclohexanol, 1-phenylethanol, 2-phenylethanol, phenol, α-naphthol, β-naphthol, o-, m- or p-cresol, 2,3-, 2,4-, 2,5-, 2,6- or 3,5-xylenol, o-, m- or p-chlorophenol, o-, m- or p-fluorophenol, 4-methoxyphenol, 6-bromo-α-naphthol, 6-bromo-β-napathol, 2-methoxy-4-n-propylphenol, p-chlorobenzyl alcohol, p-fluorobenzyl alcohol, pentafluorobenzyl alcohol, ethylene glycol, 1,3-propanediol, 1,4-butanediol, trimethylpropane, pentaerythritol, ammonia, methylamine, ethylamine, n-propylamine, isopropylamine, n-butylamine, isobutylamine, benzylamine, dimethylamine, diethylamine, n-butylmethylamine, dibenzylamine, cyclohexylamine, N-methylcyclohexylamine, N-ethylcyclohexylamine, aniline, N-methylaniline, N-ethylaniline, N-benzylaniline, o-, m- or p-chloroaniline, o-, m- or p-fluoroaniline, o-, m- or p-methylaniline, 2,4-, 2,6- or 3,5-dimethylaniline, 2,3-, 2,4-, 2,5-, 3,4- or 3,5-dichloroaniline, 2,4,5- or 2,4,6-trichloroaniline, 3,5-bis-(trifluoromethyl)-aniline, ethylenediamine or hexamethylenediamine.

3. A process according to claim 1 wherein said H-acid nucleophilic compound is employed in at least an equimolar amount relative to the unsaturated carboxamide.

4. A process according to claim 3 wherein said H-acid nucleophilic compound is employed in an amount of 1.05 to 5 mols per mol of unsaturated carboxamide.

5. A process according to claim 1 wherein said H-acid nucleophilic compound is selective from the group consisting of methanol, glycol monomethyl ether, phenol, ethanol, cyclohexanol, benzyl alcohol, 3,5-dichloroaniline, N-methylaniline and 3,5-bis-(trifluoromethyl)-aniline.

6. A process according to claim 1 wherein said unsaturated carboxamide is selected from the group consisting of crotonic acid diethylamide, pent-3-enoic acid diethylamide and pent-3-enanilide.

7. A process according to claim 1 carried out in the absence of a tertiary nitrogen base.

8. A process according to claim 1 wherein the process is carried out in the presence of a tertiary nitrogen base.

9. A process according to claim 8 wherein said tertiary nitrogen base is selected from the group consisting of pyridine, isoquinoline, β-picoline, γ-picoline, 3,5-lutidine, 4-ethylpyridine and 4-benzylpyridine.

10. A process according to claim 8 wherein said tertiary nitrogen base is pyridine.

11. A process according to claim 1 wherein said carbon monoxide is in a mixture with 0.5 to 10% by volume of hydrogen, based upon the volume of said carbon monoxide.

12. A process according to claim 1 wherein the process is carried out at a carbon monoxide pressure of 20 to 4,000 bar at a temperature of 90° to 220° C.

13. A process according to claim 1 wherein said unsaturated carboxamide is crotonic acid diethylamide.

14. A process according to claim 13 wherein said H-acid neucleophilic compound is methanol.

15. A process according to claim 13 wherein said H-acid neucleophilic compound is glycol monomethyl ether.

16. A process according to claim 13 wherein said H-acid neucleophilic compound is phenol.

17. A process according to claim 13 wherein said H-acid neucleophilic compound is ethanol.

18. A process according to claim 13 wherein said H-acid neucleophilic compound is cyclohexanol.

19. A process according to claim 13 wherein said H-acid neucleophilic compound is benzyl alcohol.

20. A process according to claim 13 wherein said H-acid neucleophilic compound is 3,5-dichloroaniline.

* * * * *